(12) United States Patent
Kropfgans et al.

(10) Patent No.: US 6,750,361 B2
(45) Date of Patent: Jun. 15, 2004

(54) CLEAVAGE OF CYCLIC ORGANOSILANES IN THE PREPARATION OF AMINOFUNCTIONAL ORGANOALKOXYSILANES

(75) Inventors: Frank Kropfgans, Rheinfelden (DE); Hartwig Rauleder, Rheinfelden (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/159,122

(22) Filed: Jun. 3, 2002

(65) Prior Publication Data

US 2003/0009045 A1 Jan. 9, 2003

(30) Foreign Application Priority Data

Jun. 1, 2001 (DE) .......................................... 101 26 669

(51) Int. Cl.⁷ .................................................. C07F 7/00
(52) U.S. Cl. ...................................... 556/413; 556/400
(58) Field of Search .................................. 556/400, 413

(56) References Cited

U.S. PATENT DOCUMENTS

| | | | | |
|---|---|---|---|---|
| 412,830 | A | * 3/1976 | Vahkensieck et al. | |
| 4,234,503 | A | * 11/1980 | Kappler et al. | 556/413 |
| 5,527,937 | A | 6/1996 | Standke et al. | |
| 5,536,860 | A | 7/1996 | Monkiewicz et al. | |
| 5,616,755 | A | * 4/1997 | Seiler et al. | 556/413 |
| 5,616,762 | A | 4/1997 | Kropfgans et al. | |
| 5,629,400 | A | 5/1997 | Standke et al. | |
| 5,646,325 | A | 7/1997 | Monkiewicz et al. | |
| 5,654,459 | A | 8/1997 | Kropfgans et al. | |
| 6,150,551 | A | 11/2000 | Kropfgans et al. | |
| 6,177,584 | B1 | 1/2001 | Loewoenberg et al. | |
| 6,242,628 | B1 | 6/2001 | Kropfgans et al. | |
| 6,423,858 | B1 | 7/2002 | Schwarz et al. | |

FOREIGN PATENT DOCUMENTS

| | | |
|---|---|---|
| DE | 1 023 462 | 1/1958 |
| DE | 27 49 316 | 8/1978 |
| DE | 27 49 316 | 5/1979 |
| DE | 27 53 124 | 6/1979 |
| EP | 0 702 017 A1 | 3/1996 |
| EP | 0 905 137 A2 | 3/1999 |
| EP | 0 905 137 A3 | 10/1999 |
| EP | 1 209 162 | 5/2002 |

OTHER PUBLICATIONS

CA: 82:57805 abs of Khimiko–Farmatsevticheskii Zhurnal by Lukevics et al 8(10) 1974.*
CA:94:156998 abs of Huaxue Xuebao by Wu et al 38(5) pp 484–8 1980.*
CA:93:150371 abs of SU 724515 Mar. 1980.*
Tsai, Tsu–Tzu et al; "Synthesis of 1–aza–2–silacyclopentane compounds" Journal of Organic Chemistry (1972), 37(4), 596–600.

* cited by examiner

Primary Examiner—Jean F. Vollano
(74) Attorney, Agent, or Firm—Oblon, Spivak, McClelland, Maier & Neustadt, P.C.

(57) ABSTRACT

An aminofunctional organoalkoxysilane of formula I $$R_2N-(CH_2)_y-Si(OR^1)_{3-n}R^2_n \quad (I),$$

wherein the R groups bonded to nitrogen are identical or different and each individual R group is hydrogen, an alkyl radical having from 1 to 4 carbon atoms, an aryl radical or an arylalkyl radical, $R^1$ is an alkyl radical having from 1 to 8 carbon atoms or an aryl radical, $R^2$ is an alkyl radical having from 1 to 8 carbon atoms or an aryl radical, y is 2, 3 or 4 and n is 0, 1 or 2, is prepared by a process comprising:

reacting a chlorofunctional organoalkoxysilane of formula II $$Cl-(CH_2)_y-Si(OR^1)_{3-n}R^2_n \quad (II),$$

wherein $R^1$, $R^2$, y and n are as defined above, with ammonia or an organic amine of formula III $$HNR_2 \quad (III),$$

wherein the two R groups are identical or different and each is defined as described above;

separating organic amine hydrochloride or ammonium chloride by-product which is formed in the reaction;

distilling the resulting crude product, thereby preparing an aminofunctional organoalkoxysilane or the product fraction of an aminofunctional organoalkoxysilane; and treating the aminofunctional organoalkoxysilane or the product fraction of an aminofunctional organoalkoxysilane with an alcohol.

11 Claims, No Drawings

CLEAVAGE OF CYCLIC ORGANOSILANES IN THE PREPARATION OF AMINOFUNCTIONAL ORGANOALKOXYSILANES

BACKGROUND OF THE INVENTION

1. Field of the Invention

The present invention relates to a process for preparing aminofunctional organoalkoxysilanes by reacting chlorofunctional organoalkoxysilanes with ammonia or an organic amine, separating the ammonium chloride or organic amine hydrochloride by-product formed, and working-up the resulting crude product by distillation. Aminofunctional organoalkoxysilanes will hereinafter also be referred to as aminosilanes.

2. Description of the Background

Aminosilanes have a wide range of uses. They are employed, for example, for the sizing of glass fibers and are employed as processing aids in the foundry industry. They likewise serve as adhesion promoters for storage-stable resins.

It is known that aminofunctional organoalkoxysilanes can be prepared from chlorofunctional organoalkoxysilanes and ammonia or organic amines (DE-C 10 23 462, DE-C 27 49 316, DE-C 27 53 124, German patent application 100 58 620.1).

When aminofunctional organoalkoxysilanes are heated, an alkoxy group on the silicon atom is eliminated to form the alcohol corresponding to the alkoxy group together with a cyclic compound containing the Si—N structural element, for example:

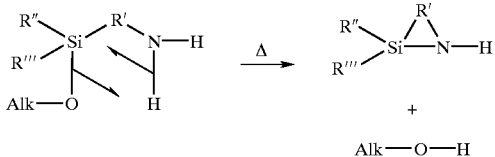

As a consequence, distillation of an aminofunctional organoalkoxysilane results in a decrease in the content of the linear aminofunctional organoalkoxysilane and a simultaneous increase in the abovementioned cyclic compound. This is a disadvantage because the desired high content of linear aminofunctional organoalkoxysilane, as is necessary, for example, for applications of the aminofunctional organoalkoxysilane in sizes in glass fiber production, is no longer achieved.

SUMMARY OF THE INVENTION

Accordingly, one object of the present invention is to provide a way of reducing the content of cyclic compounds in aminofunctional organoalkoxysilanes.

Briefly, this object and other objects of the present invention as hereinafter will become more readily apparent can be attained by a process for preparing an aminofunctional organoalkoxysilane of formula I $$R_2N-(CH_2)_y-Si(OR^1)_{3-n}R^2_n \qquad (I),$$

wherein the R groups bonded to nitrogen are identical or different and each individual R group is hydrogen, an alkyl radical having from 1 to 4 carbon atoms, an aryl radical or an arylalkyl radical, $R^1$ is an alkyl radical having from 1 to 8 carbon atoms or an aryl radical, $R^2$ is an alkyl radical having from 1 to 8 carbon atoms or an aryl radical, y is 2, 3 or 4 and n is 0, 1 or 2, comprising:

reacting a chlorofunctional organoalkoxysilane of formula II

wherein $R^1$, $R^2$, y and n are as defined above, with ammonia or an organic amine of formula III

wherein the two R groups are identical or different and each is defined as described above;

separating organic amine hydrochloride or ammonium chloride by-product which is formed in the reaction;

distilling the resulting crude product, thereby preparing an aminofunctional organoalkoxysilane or the product fraction of an aminofunctional organoalkoxysilane; and treating the aminofunctional organoalkoxysilane or the product fraction of an aminofunctional organoalkoxysilane with an alcohol.

DETAILED DESCRIPTION OF THE PREFERRED EMBODIMENTS

It has surprisingly been found that aminofunctional organoalkoxysilane contaminated with a cyclic compound or the product fraction of an aminofunctional organoalkoxysilane obtained in the production process by work-up by distillation can be after-treated in a simple fashion by addition of an alcohol thereto, by which means the proportion of cyclic compounds can be reduced in an advantageous manner to <0.1% (GC-WLD-% by area) down to the detection limit of the cyclic compound.

It is also surprising that the above-mentioned cyclic compound can be cleaved again by addition of alcohol and, if necessary, moderate heating so that the loss of linear product can be reversed in a simple manner. In this cleavage reaction, the Si—N bond of the cyclic compound is opened with addition of the alkoxy group of the alcohol added onto the Si atom to reform the alkoxyfunction and linear aminofunction, with the hydrogen of the alkyl added being transferred to the nitrogen of the aminofunction.

Furthermore, the present process is particularly economical since product losses generally do not occur.

The process of the present invention is preferably employed for preparing the following aminofunctional organoalkoxysilanes or freeing the aminofunctional organoalkoxysilanes of cyclic compounds:
3-aminopropyltrimethoxysilane,
N-methyl-3-aminopropyltrimethoxysilane,
3-aminopropyltriethoxysilane,
3-aminopropylmethyldiethoxysilane,
N-aminoethyl-3-aminopropyltrimethoxysilane,
N-aminoethyl-3-aminopropylmethyldimethoxysilane,
N-aminoethyl-3-aminopropyltrimethoxysilane.

However, the list of aminofunctional organoalkoxysilanes of cyclic compounds above does not exclude other aminofunctional organoalkoxysilanes of formula I from the scope of the present invention.

In the process of the invention, the procedure employed generally is to add an alcohol to the aminosilane contaminated with cyclic aminosilanes and treating the material for some time at a comparatively mild temperature, in particular at a temperature in the range from 20 to 60° C., with the treatment preferably being conducted for 30 minutes to 6 hours, particularly preferably for 2 to 4 hours. However, the treatment of the invention can also be conducted for a longer period of time.

The alcohol employed in the process of the invention is preferably the alcohol corresponding to the alkoxy group of the aminofunctional organoalkoxysilane. The alcohol can be added in solid, liquid or gaseous form to the aminosilane to be treated, with the aminosilane or the product fraction appropriately being at a temperature ranging from 20 to 60° C. The alcohol is preferably added in liquid form, and particularly preferably is methanol, ethanol,—or i-propanol or an alcohol corresponding to the alkoxy group of the silane.

Furthermore, the alcohol is preferably added in an amount up to the stochiometric amount, based on the amount of cyclic silane present in the aminosilane or in the product fraction, in the process of the invention.

In particular, the treatment with alcohol of the invention of a given aminosilane is conducted at a temperature in the range from 20 to 60° C., preferably in the range from 25 to 55° C., particularly preferably in the range from 30 to 50° C. For this purpose, the aminosilane or the product fraction to be treated of the invention can be additionally heated. The treatment of the invention is appropriately conducted while the respective aminosilane or product fraction is being stirred or circulated by pumping.

Aminosilanes which have been treated by the process of the invention have an advantageously low content of cyclic aminosilane of <0.1 GC-WLD-% by area.

The disclosure of German priority application Serial No. 10126669.3 filed Jan. 6, 2001 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A process for preparing an aminofunctional organoalkoxysilane of formula I

    (I), wherein the R groups bonded to nitrogen are identical or different and each individual R group is hydrogen, an alkyl radical having from 1 to 4 carbon atoms, an aryl radical or an arylalkyl radical, $R^1$ is an alkyl radical having from 1 to 8 carbon atoms or an aryl radical, $R^2$ is an alkyl radical having from 1 to 8 carbon atoms or an aryl radical, y is 2, 3 or 4 and n is 0, 1 or 2, comprising:

reacting a chlorofunctional organoalkoxysilane of formula II

    (II), wherein $R^1$, $R^2$, y and n are as defined above, with ammonia or an organic amine of formula III

    (III), wherein the two R groups are identical or different and each is defined as described above;

separating organic amine hydrochloride or ammonium chloride by-product which is formed in the reaction;

distilling the resulting crude product to produce a distillate comprising aminofunctional organoalkoxysilane of formula I and a cyclic aminosilane; and converting the cyclic aminosilane to the aminofunctional organoalkoxysilane by treating the distillate with a treating agent that consists essentially of an alcohol.

2. The process as claimed in claim 1, wherein the alcohol is the alcohol which corresponds to the alkoxy functional group of the aminofunctional organoalkoxysilane of formula I.

3. The process as claimed in claim 1, wherein the treatment of the distillate with alcohol is conducted at a temperature in the range from 20 to 60° C. for 0.5 to 6 hours.

4. The process as claimed in claim 3, wherein the treatment of the distillate with alcohol is conducted at a temperature in the range from 25 to 55° C.

5. The process as claimed in claim 4, wherein the treatment of the distillate with alcohol is conducted at a temperature in the range from 30 to 50° C.

6. The process as claimed in claim 1, wherein the alcohol is added in solid, liquid or gaseous form and the distillate is at a temperature ranging from 20 to 60° C.

7. The process as claimed in claim 1, wherein the alcohol is added in an amount up to the stoichiometric amount, wherein the stoichiometric amount is based on the amount of cyclic silane present in the distillate.

8. The process as claimed in claim 1, wherein the treatment with alcohol is conducted while the distillate is being stirred or circulated by pumping.

9. The process as claimed in claim 1, wherein the distillate is heated to conduct the alcohol treatment of the distillate.

10. The process as claimed in claim 1, wherein the the cyclic aminosilane content of the distillate is <0.1 GC-TCD % by area.

11. The process as claimed in claim 1, wherein the aminofunctional organoalkoxysilane is 3-aminopropyltrimethoxysilane, N-methyl-3-aminopropyltrimethoxysilane, 3-aminopropyl-triethoxysilane, 3-aminopropylmethyldiethoxysilane, N-aminoethyl-3-aminopropyltrimethoxysilane, N-aminoethyl-3-aminopropylmethyldimethoxysilane or N-aminoethyl-3-aminopropyltrimethoxysilane.

* * * * *